(12) United States Patent
Biedermann et al.

(10) Patent No.: US 8,267,976 B2
(45) Date of Patent: *Sep. 18, 2012

(54) BONE SCREW AND BONE SCREW WITH HOLDING ELEMENT

(75) Inventors: Lutz Biedermann, VS-Villingen (DE); Jürgen Harms, Karlsruhe (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/775,745

(22) Filed: May 7, 2010

(65) Prior Publication Data

US 2010/0286732 A1 Nov. 11, 2010

Related U.S. Application Data

(63) Continuation of application No. 10/680,706, filed on Oct. 6, 2003, now Pat. No. 7,736,381.

(30) Foreign Application Priority Data

Oct. 4, 2002 (DE) .................................. 102 46 386

(51) Int. Cl.
*A61B 17/86* (2006.01)

(52) U.S. Cl. ....................................................... 606/301

(58) Field of Classification Search ................. 606/300, 606/301, 304–309, 318, 319
See application file for complete search history.

(56) References Cited

U.S. PATENT DOCUMENTS

| 1,394,608 A | 10/1921 | Davern |
| 1,988,813 A | 1/1935 | Seguin |
| 2,993,950 A | 7/1961 | Forman |
| 4,022,099 A | 5/1977 | Ballantyne |
| 4,456,005 A | 6/1984 | Lichty |
| 4,484,570 A | 11/1984 | Sutter et al. |
| 4,653,489 A | 3/1987 | Tronzo |
| 4,705,027 A | 11/1987 | Klaue |

(Continued)

FOREIGN PATENT DOCUMENTS

DE 199 49 285 A1 5/2001
(Continued)

OTHER PUBLICATIONS

Kaiser et al., "Zur Verfahrenswahl bei Pertrochantaeren Femurfrakturen," Unfallchirurgie, Urban & Vogel, Apr. 1999, vol. 25, No. 2, pp. 50-54, including English Abstract, ISSN 1439-0590.

(Continued)

*Primary Examiner* — Nicholas Woodall
(74) *Attorney, Agent, or Firm* — Christie, Parker & Hale, LLP

(57) ABSTRACT

A bone screw is provided, with a thread section (2) of tubular construction having a tip (3) at its first end and a second end opposite the latter. The tubular thread section (2) comprises a bone thread (22) on its outer wall, and the wall of the thread section (2) comprises a plurality of recesses (21). The bone screw further includes a holding element (4, 6) with a first section (41, 61) for connection to the thread section (2) and with a rod-like second section (43, 63) which in the inserted state of the holding element (4, 6) protrudes beyond the second end of the thread section (2). A stop is provided for limiting the distance of insertion of the holding element (4, 6) in the thread section (2). The holding element (4, 6) comprises an element (44, 64) at its free end for engagement with a screw-in tool.

13 Claims, 3 Drawing Sheets

U.S. PATENT DOCUMENTS

| | | | |
|---|---|---|---|
| 4,708,132 | A | 11/1987 | Silvestrini |
| 4,940,467 | A | 7/1990 | Tronzo |
| 5,030,052 | A | 7/1991 | Anderson et al. |
| 5,057,111 | A | 10/1991 | Park |
| 5,092,866 | A | 3/1992 | Breard et al. |
| 5,100,405 | A | 3/1992 | McLaren |
| 5,167,664 | A | 12/1992 | Hodorek |
| 5,549,610 | A | 8/1996 | Russell et al. |
| 5,645,546 | A | 7/1997 | Fard |
| 5,713,901 | A | 2/1998 | Tock |
| 5,964,761 | A | 10/1999 | Kambin |
| 6,048,343 | A | 4/2000 | Mathis et al. |
| 6,053,916 | A | 4/2000 | Moore |
| 6,402,757 | B1 | 6/2002 | Moore, III et al. |
| 6,471,707 | B1 | 10/2002 | Miller et al. |
| 6,517,543 | B1 | 2/2003 | Berrevoets et al. |
| 6,755,834 | B2 | 6/2004 | Amis |
| 6,902,567 | B2 | 6/2005 | Del Medico |
| 2001/0000186 | A1 | 4/2001 | Bramlet et al. |
| 2001/0021852 | A1 | 9/2001 | Chappius |
| 2001/0049528 | A1 | 12/2001 | Kubota |
| 2002/0055783 | A1 | 5/2002 | Tallarida et al. |
| 2004/0015172 | A1 | 1/2004 | Biedermann et al. |
| 2004/0172030 | A1 | 9/2004 | Tipirrneni |
| 2005/0101958 | A1 | 5/2005 | Adam |
| 2005/0143735 | A1 | 6/2005 | Kyle |

FOREIGN PATENT DOCUMENTS

| | | |
|---|---|---|
| DE | 100 55 891 A1 | 6/2002 |
| EP | 1 222 899 A2 | 7/2002 |
| FR | 2 820 630 | 8/2002 |
| JP | 04-506615 A | 11/1992 |
| JP | 2001-17440 | 1/2001 |
| WO | WO 88/03781 | 6/1988 |
| WO | WO 02/38054 A2 | 5/2002 |

OTHER PUBLICATIONS

Patent Abstracts of Japan, Publication No. 2001-017440, Published on Jan. 23, 2001, in the name of Hata Morishige et al.

Boothroyd et al., Product Design for Manufacture and Assembly, 1994, Marcel Dekker Inc., pp. 64 and 77.

European Search Report dated Sep. 4, 2007 for EPO Application No. 07014106.4, European Search Report mailed Sep. 17, 2007; Biedermann Motech GmbH (6 pp.).

Fig. 4
Fig. 5
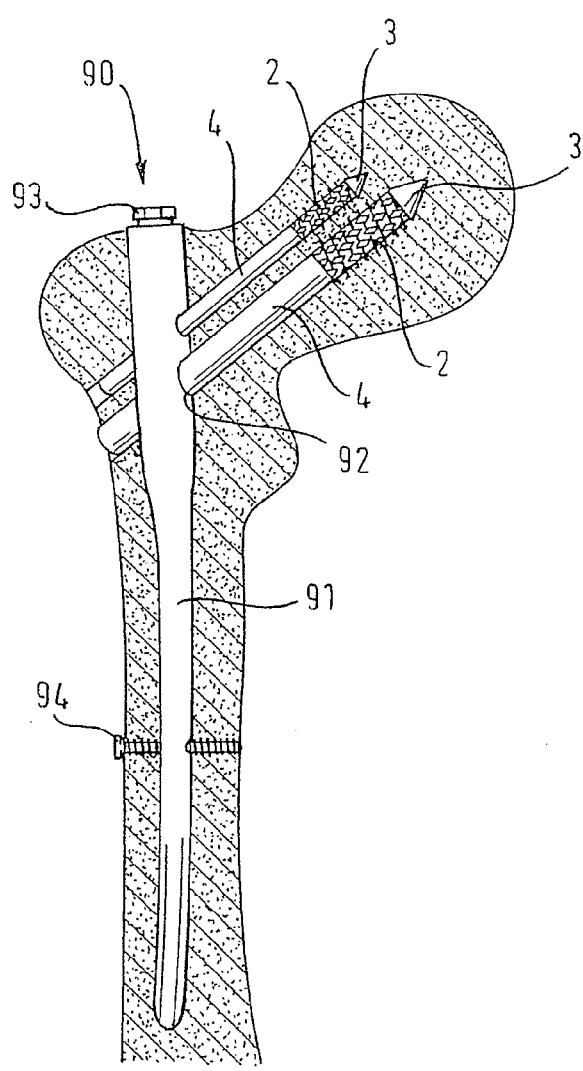
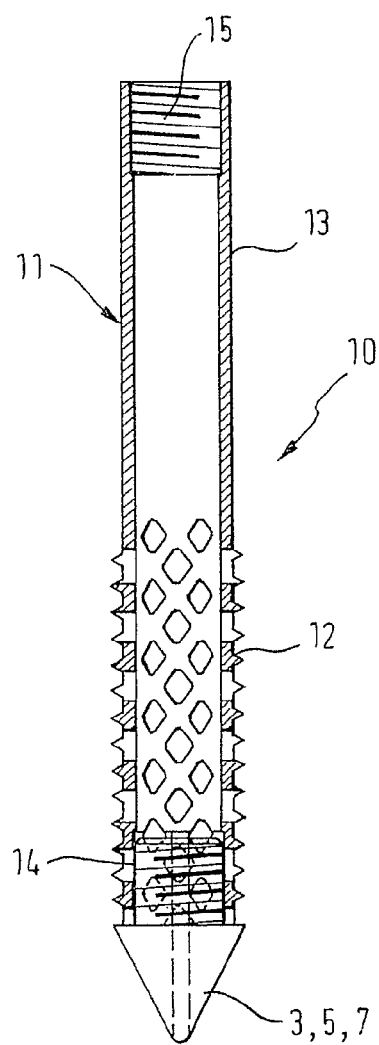

BONE SCREW AND BONE SCREW WITH HOLDING ELEMENT

CROSS-REFERENCE TO RELATED APPLICATION(S)

This application is a continuation of Application No. 10/680,706 filed Oct. 6, 2003 now U.S. Pat. No. 7,736,381, which claims priority to and the benefit of German Patent Application No. 102 46 386.7 filed on Oct. 4, 2002, the disclosures of which are fully incorporated herein by reference.

FIELD OF THE INVENTION

The present invention relates to a bone screw, in particular to a bone screw with a thread section having a periphery with an open net-like or mesh-like structure.

BACKGROUND OF THE INVENTION

A bone screw having a tubular wall with a plurality of recesses is described in DE 100 55 891 A1. It includes a thread section, a tip at one end and a head for engagement with a screwdriver at the other end. The thread section of the tubular wall also comprises the plurality of recesses.

This bone screw can be used e.g. in the treatment of osteoporotic fractures. On account of the open mesh (or net-like) design of the screw, fusion with surrounding bone material can take place.

A problem can be encountered when the position of the fracture in the bone, which e.g. in the hipbone is far away from the surface from which the screw is screwed in. In such situation, for reliable fixation, precise positioning of the bone screw is required and, sometimes, a mechanical connection to external and/or internal bracing implants also may be required.

A bone screw system including a cannulated bone screw and an adapter designed to be releasably coupled to the screw is known from U.S. Pat. No. 6,048,343. The bone screw has a head with a diameter which is larger than the diameter of the shaft of the screw. The largest diameter of the adapter is also greater than the diameter of the shaft of the bone screw. Thus the bone screw cannot be placed at a fracture which is at a location far away from the surface of the bone. DE 199 49 285 A1 discloses a similar bone screw system including a bone screw and an adapter.

SUMMARY OF THE INVENTION

The present invention provides a bone screw with a thread section having a periphery with an open mesh (or net-like) structure and a bone fixation device with improved properties. Preferred bone screws of the present invention can be positioned precisely and, optionally, also can be connected to external and/or internal bracing implants.

In accord with one embodiment of the present invention, a bone screw comprises a thread section of tubular construction having a tip at its first end, a second end opposite the latter, and a holding element with a first section for connection to the second end of the thread section and a rod-like second section which, in the inserted state of the holding element, protrudes beyond the second end of the thread section. The tubular thread section comprises a bone thread on its outer wall and the outer wall of the thread section comprises a plurality of recesses providing an open mesh structure. Preferably, a stop is provided for limiting the distance of insertion of the holding element into the thread section.

In another embodiment of the invention, the bone screw comprises a thread section of tubular construction having a tip at its first end and a second end opposite the latter and, adjoining the second end of the thread section, a section free of bone thread and integral with the thread section. At the end of the adjoining section free of bone thread opposite the tip, preferably, a means for engagement with a screw-in tool and/or a means for attaching a fixation element is provided. The tubular thread section comprises a bone thread on its outer wall and the wall of the thread section comprises a plurality of recesses providing an open mesh structure.

In a preferred embodiment, the fixation element comprises a fixation plate with a hole or recess through which the free end of the rod-like holding element can be passed, and the attaching means comprises a nut for screwing onto the holding element from its free end for fixing the plate.

The invention also provides a bone fixation device comprising at least one bone screw as described herein and a marrow nail for fixing a bone, the marrow nail having a borehole through which the free end of the rod-like holding element can be passed.

Certain preferred embodiments of the bone screws of the present invention comprise one or more of the following (wherein references to the drawings are provided as merely exemplary): the thread section 2 of tubular construction comprises an internal thread section 24 at its second end and the first section 41, 61 of the holding element 4, 6 comprises an external thread for screwing into the internal thread section 24; the connection between the holding element 4, 6 and the thread section 2 is made in the form of an interference fit; the holding element 4, 6 comprises an element 44, 64 at its free end for engagement with a screw-in tool; the stop is provided in the form of a shoulder 42, 62 between the first section 41, 61 and the second section 43, 63 of the holding element; the stop is provided in the tubular thread section 2 of the bone screw 1; the rod-like section 43, 63 of the holding element 4, 6 comprises an external thread for screwing on a nut 83 from the free end of the holding element 4, 6; the thread section 2 of tubular construction comprises an internal thread section 23 at its first end; the thread section 2 of tubular construction comprises an internal thread section 23 that extends over the whole length of the thread section 2 of the tubular construction and the tip 3, 5, 7 at the first end of the thread section 2 can be screwed into this internal thread section 23; the internal thread section 23, 24 is designed and structured as a metric or inch thread; the tip 7 is designed and structured as a self-tapping tip; the tip 5 is cannulated (i.e., comprises a cannula); the holding element 6 is cannulated; and/or the length of the section 13 free of bone thread is the same as or greater than that of the thread section 12.

The invention further provides a holding element 4, 6 for attaching to a bone screw, wherein the bone screw comprises a tip at its first end and, at the second end opposite the latter, a section for connection to the holding element. The holding element comprises a first section 41, 61 for connection to the bone screw, a rod-like second section 43, 63 and, preferentially, a stop for limiting the distance of insertion of the holding element 4, 6 into the bone screw. Thus, when the holding element is inserted into the bone screw, the rod-like second section 43, 63 of the holding element 4, 6 in the inserted state protrudes beyond the second end of the bone screw.

Preferably, the holding element comprises an external thread for screwing into an internal thread section of the bone screw or the connection between the holding element and the bone screw is made in the form of an interference fit.

The bone screw according to preferred embodiments of the invention has an advantage that it can be immersed to the required location in the bone. Thus, it can fulfil its function as a tension element, without a part protruding from the bone (for example, see FIG. 3b).

The invention also provides a method for repairing a bone having a fracture. The method comprises providing a bone screw as described herein, fully introducing the bone screw into the bone and positioning the bone screw at the place of fracture, and attaching the holding element to a bone fixation device. Preferably, the bone fixation device comprises a plate or a marrow nail. In preferred embodiments, before attaching the bone fixation device, the method also includes removing the holding element from the bone screw, applying a filler material into the interior of the thread section of the bone screw and reconnecting the holding element to the thread section.

Bone cement or reagents can be placed precisely by means of the bone screw.

BRIEF DESCRIPTION OF THE DRAWINGS

Further characteristics and advantages of the invention are shown by the description of embodiments with the aid of the attached drawings wherein:

FIG. 4 illustrates a view of a combination of the bone screw with a marrow nail;

FIG. 5 illustrates a bone screw according to another embodiment of the present invention.

DETAILED DESCRIPTION OF THE INVENTION AND PREFERRED EMBODIMENTS

A bone screw according to a preferred embodiment of the present invention now will be described with reference to FIGS. 1 and 2. Part of the bone screw is shown in section in FIG. 2 to improve the clarity.

Figure 1:
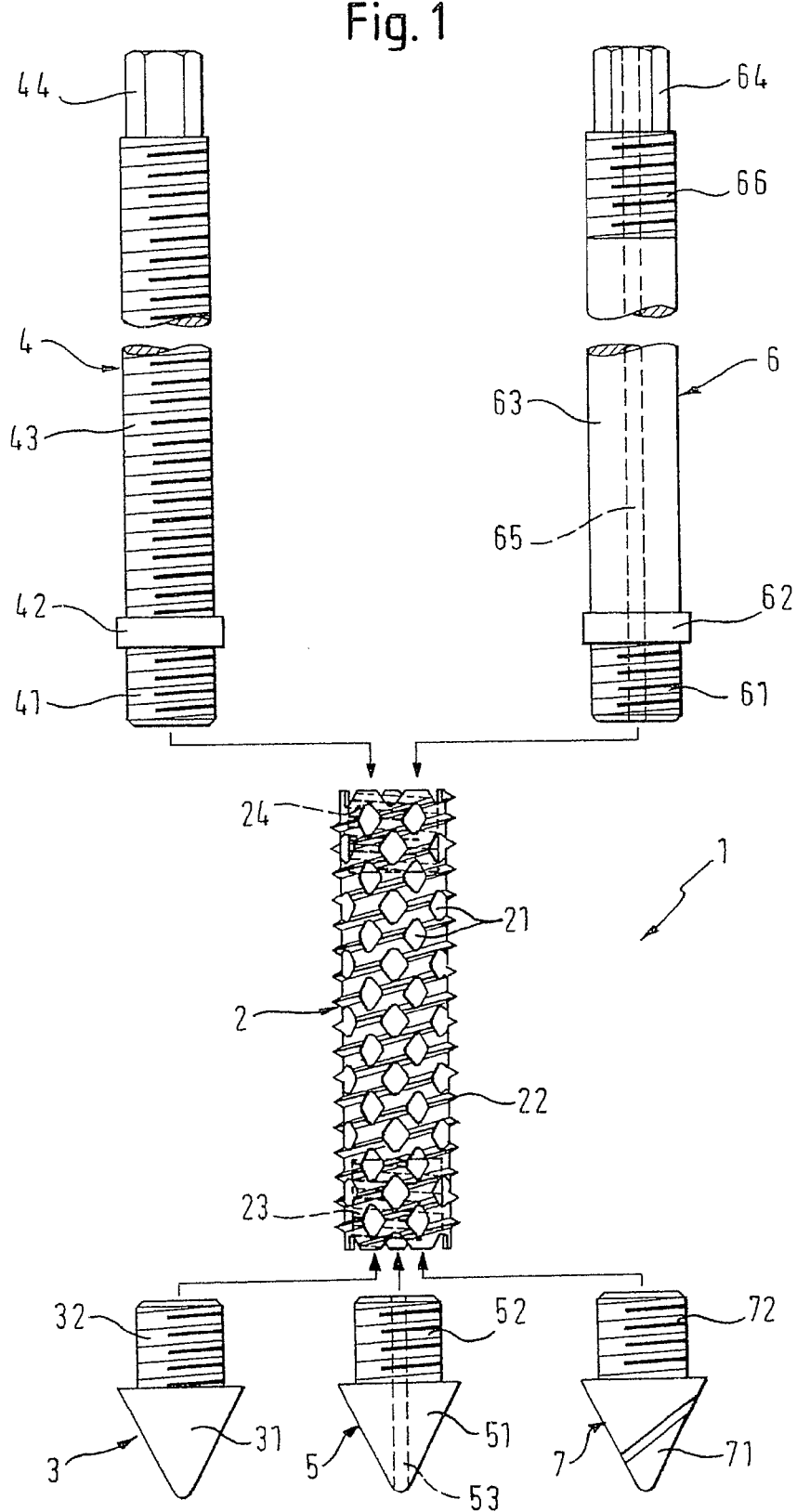
FIG. 1 illustrates an exploded view with several embodiments of a modular structure of a bone screw according to the present invention.
Figure 2:
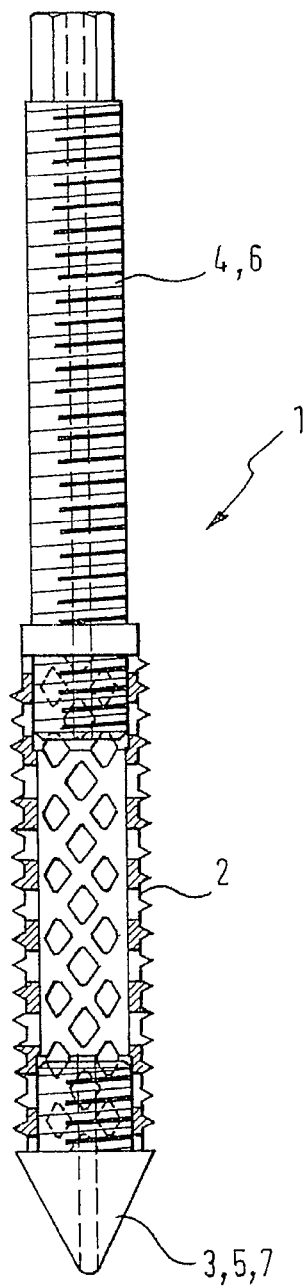
FIG. 2 illustrates a bone screw, as shown in FIG. 1, in the assembled state.

The modular bone screw shown in FIGS. 1 and 2 includes a thread section 2, a tip 3 and a holding element 4. The thread section 2 is of tubular construction and contains in its wall a plurality of recesses 21 which are diamond-shaped in the embodiment as shown and provide an open mesh structure. The diamond-shaped recesses are oriented in such a way that an axis of symmetry extends parallel to the axis of symmetry or longitudinal axis of the tube respectively. The diamonds also are staggered from each other.

On the outer surface of the wall there is provided a so-called bone thread 22 which corresponds in shape to that of the usual bone screws that are well known to those skilled in the art. On the inner surface of the wall, the tubular thread section 2 comprises at each of its two ends an internal thread 23, 24, e.g., a metric thread.

The tip 3 includes a shank portion 32 and the actual tip portion 31 having tapered sides. In the embodiment shown, the shank 32 comprises an external thread which corresponds to the internal thread 23 of the tubular thread section 2 for connection of the tip 3 to the thread section 2, as shown in FIG. 2.

The holding element 4 comprises at a first end a first section 41 with an external thread which corresponds to the internal thread 23 of the tubular thread section 2 for connection of the holding element 4 to the thread section 2, as shown in FIG. 2. At the end of the thread section 41, a stop 42 is provided in the form of a shoulder or annular projection from the outer surface. The stop limits the screw-in distance when assembling the holding element 4 with the thread section 2. As can be seen in particular from FIG. 2, the outer diameter of the annular projection of stop 42 preferably corresponds to the outer diameter of the tubular thread section 2, so that it does not form an obstacle in the bone opening when the bone screw is screwed into the bone.

The holding element further comprises a rod-like section 43 which, as shown in FIG. 2, protrudes beyond the second end of the thread section 2 of the assembly. The rod-like section 43 preferably is provided continuously with a metric external thread. The axial length of the rod-like second section 43 preferably is longer than that of the first section 41, which is to be screwed into the thread section 2. Due to the modular construction of the bone fixation device, the length of the holding element can be selected by the surgeon at the place of use of the bone screw in such a way that the tubular thread section 2 can be immersed to the required location in the bone.

At its free end opposite the section 41, the holding element comprises an engagement element for a screw-in tool in the form of a hexagon shaped outer surface 44. However, the engagement element can be a structure that corresponds to any standard or non-standard driving tool for turning the bone fixation assembly.

The thread section 2, the tip 3 and the holding element 4 are formed preferably from titanium. However, any other biocompatible material can be used providing it has sufficient strength properties for use in a bone fixation application.

Use of the bone screw now is described with reference to FIGS. 2 and 3. The bone screw 1, e.g., is inserted into the end of a long bone which is weakened from the inside by osteoporosis, e.g., in the neck of a femur.

The fixation device is assembled, first, by screwing the tip 3 into the tubular thread section 2. Next, the holding element 4 is screwed into the thread section 2. As a result the structure shown in FIG. 2 is obtained.

Next, as shown in FIG. 3a, the bone screw 1 composed of thread section 2, tip 3 and holding element 4 is screwed into the bone. In the process, the thread section 2 can be immersed deep in the bone and at the same time positioned precisely at the place of fracture. Then, the holding element 4 is unscrewed and removed from the thread section 2.

In a further step, such as depicted in FIG. 3b, a filler material such as bone cement or the like and/or a medicinal or growth-promoting reagent, if desired, can be injected into the interior of the thread section 2. By contrast with direct injection, the thread section 2 ensures more accurate positioning of the injection channel and more even distribution of the injected material which can exit through the recesses 21 into the adjacent sections of the bone. As a result, fixation of the bone by the screw can be improved further.

The immersed bone screw serves as a reinforcement for the bone trabeculae weakened e.g. by osteoporosis. Through the recesses 21, the bone can grow into the screw. Stabilization of the fracture point of the weakened bone, thus, takes place as a combination of tension relief and fusion.

FIG. 3c illustrates the use of an outer fixation plate 81 as a fixation device 80 for fixation of the bone. Here, after injection of the filler material, if desired, the holding element 4 is screwed back into the thread section 2. The plate 81 with a recess (or through-hole) 82 is applied to the bone in such a way that the free end of the holding element 4 extends through the recess 82, and the plate 81 is rigidly connected to the bone screw 1 by screwing a nut 83 onto the external thread of the rod-like section 43 of the holding element 4. Further, bone screws 84 can be added to serve for a stable fixation of the plate 81 to the bone. The rod-like section 43 the holding element 4 preferably can be shortened to a finished length such that it does not protrude substantially beyond the nut 83.

FIG. 4 shows a further example of application of the bone screw according to the first embodiment. With the fixation device 90, fixation of the bone takes place not by means of an outer fixation plate but, instead, by means of a marrow nail 91 introduced into the bone. The marrow nail 91 comprises at least one recess (or bore hole) 92 through which extends at least one holding element 4 of a bone screw 1. In the embodiment shown in FIG. 4, there are two bone screws 1 with different diameters. A closure screw 93 closes the marrow nail against the outside, and a locking screw 94 prevents movement in the longitudinal direction.

A second embodiment of the modular bone screw 1 shown in FIG. 1 differs from the first embodiment in that, instead of the tip 3, a cannulated tip 5 is provided. Further, in this embodiment the holding element is a cannulated holding element 6. The cannulated tip 5 differs from the tip 3 in that, in addition, a coaxial bore 53 for passage of a reagent is provided. The cannulated holding element 6 differs from the holding element 4 in that, in addition, a coaxial bore 65 is provided and in that the rod-like section 63 is not provided with a metric thread over its whole length like the rod-like section 43 in the first embodiment, but only in a partial section 66.

All other characteristics of this second embodiment match the first embodiment, and use of the device also takes place in the same way. This embodiment has the advantage that, even without unscrewing the holding element and even after installation is completed, a medicinal reagent can be introduced precisely to the desired location, e.g., by means of a syringe.

A third embodiment of the modular bone screw 1 shown in FIG. 1 differs from the first and second embodiments in that, instead of the tip 3, a self-tapping tip 7 is provided. All of the other characteristics correspond to the first or second embodiment, and use of this embodiment takes place in the same way, as well. Introduction of the bone screw into the bone can be easier by the self-tapping tip.

A fourth embodiment shown in FIG. 5 differs from the first to third embodiments shown in FIGS. 1 and 2 in the structure of the screw section. The bone screw 10, in accord with the fourth embodiment, includes a screw section 11 and a tip. The screw section 11 is of tubular construction and consists of a thread section 12 and an integral section 13 free of bone thread. Any of the tips 3, 5 and 7 described in the first to third embodiments can be used as the tip.

The thread section 12, like the thread section 2 described in the first embodiment, comprises in its circumferential wall a plurality of recesses 21 and, on its outer surface of the wall, a bone thread 22. The section 13, on the other hand, is formed without bone thread. In this embodiment as shown, no recesses are formed in the wall in the section 13, which is free of bone thread. However, in certain preferred embodiments, recesses can be provided here, too, to provide further open mesh structure.

On the inner surface of the wall, the tubular screw section 11 comprises preferably at each of its two ends a metric internal thread 14, 15. The axial length of the section 13 (free of bone thread) is selected as a function of the place of use of the bone screw in such a way that the thread section 12 can be immersed to the required location in the bone. The axial length of the section 13 also can be longer than the axial length of the thread section 12.

The tubular screw section 11 is preferably formed from titanium. However, as stated above, any other biocompatible material having suitable strength properties can be used as well.

Use of the embodiment shown in FIG. 5 also takes place in the same way as in the first to third embodiments, as described above. To screw the bone screw 10 into the bone, a holding element 4, 6 can be screwed into the internal thread 15. The holding element can be removed later or can remain as an extender. Alternatively, a head with an engagement element can be inserted using thread 15 for engaging and cooperating with a screw-in tool. The free end of the section 13 without bone thread can also itself comprise an engagement element for a screw-in tool, e.g., a cross recess.

The embodiments described are only examples. Thread section, tip and holding element can be combined with each other not only as described in the embodiments, but in many ways by those skilled in the art after considering this disclosure. This modular structure allows adaptation to the most varied demands.

The stop for limiting the distance of screwing the holding element 4, 6 into the thread section 2 can be provided in the tubular thread section 2 instead of on the holding element 4, 6, e.g. at the end of the internal thread 24.

The holding element 4, 6 can be formed such that the rod-like section 43, 63 comprises an external thread over its whole length as in the first embodiment, or only in a partial section as in the second embodiment. Alternatively, the rod-like section 43, 63 can also be formed completely without an external thread. Further, the diameter of the rod-like section 43, 63 can, as shown in FIGS. 1 and 2, be the same as that of the first section 41, 61 of the holding element 4, 6, but it can also have a different, preferably smaller diameter. In addition, the rod-like section can be made of a tubular construction, similar to the thread section.

The holding section 14 according to the fourth embodiment too can have an external thread over its whole length or only in a partial section as in the second embodiment.

Instead of the outer hexagon section 44, 64, any other shape or type of engagement element for cooperating with a screw-in tool can be provided. Thus, the free end of the holding element 4, 6 alternatively can have, e.g., a recess for an Allen type wrench, too. The holding element 4, 6 also can be designed without an engagement element 44, 64 for a screw-in tool. The bone screw is then screwed in with a suitable tool which engages with the rod-like section 43.

The thread sections 23, 24, 41, 43, 61, 66, 14 and 15 have been described sometimes herein as metric in the embodiments. Alternatively, the threads can be inch threads or in some other suitable form.

Instead of the internal threads 23 and 24 or 14 and 15, a single internal thread which extends over the whole length of the thread section 2 or screw section 11 can be formed (this also can be applied for holding element sections that are a tubular structure). This has the advantage that the tubular material can be manufactured in long pieces and cut to any length, so that bone screws of the desired length can be made at the site of use, and so stockkeeping of various lengths of components can be substantially reduced.

As an alternative to the diamond-shaped recesses 21, other shapes of opening can be provided, in particular, round openings.

The tip 3, 5, 7 can be connected to the thread section 2 or 12 not only by screwing in. Alternatively, the first end of the thread section 2 or 12 and the shank 32, 52, 72 of the tip 3, 5, 7 can be formed without the respective threads and defined in their dimensions such that the tip 3, 5, 7 is rigidly connected to the thread section 2 or 12 in a snug fit or interference fit. Further, alternatively, the tip 3, 5, 7 can be connected rigidly to the thread section 2 or 12 in any other way. The tip and thread section also can be formed integrally in one piece.

The holding element 4, 6, too, can be connected rigidly to the thread section 2 or 12 in a snug (or interference) fit or in any other way.

Figure 3:
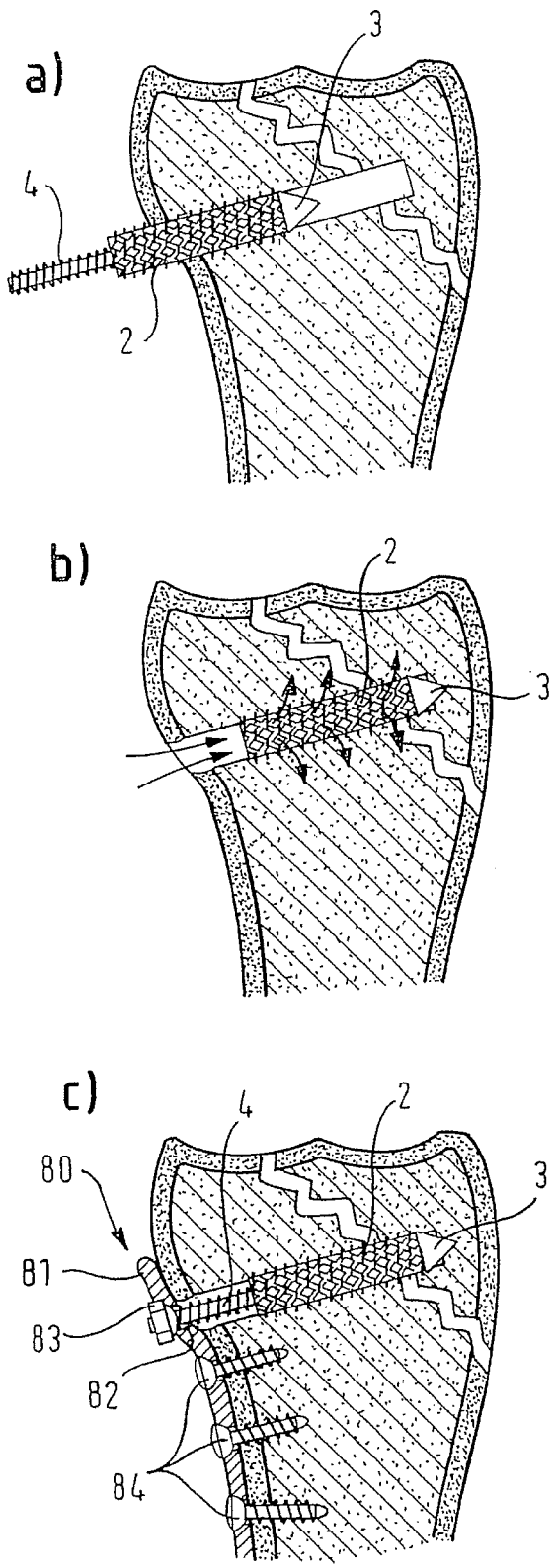
FIG. 3a to FIG. 3c illustrate a sequence of steps for attaching an outer plate to a bone.

As an alternative to the procedure shown in FIGS. 3 a) to c), the tubular thread section 2 can be filled, e.g., with bone material before screwing on the holding element. Then, the screw is immersed.

The screw can also remain in the immersed state without being connected to a plate via a holding element.

The combination of tension relief and fusion described above with reference to FIGS. 3a)-3c) can of course be carried out not only in the femur, as mentioned as an example, but also in any other bones, e.g., the tibia, etc.

The bone screw 1, 10 is not suitable only, as shown in the practical examples, for introduction into long bones. It can be used e.g. in vertebrae or other bones as well.

The holding element 4, 6 can be used not only in combination with the tubular thread section 2, but also with any other form of bone screws which can be, e.g., solid or cannulated. The connection to other forms of bone screws is made in the same or a similar way as the connection to the thread section 2 described above.

This invention has been described in detail including the preferred embodiments thereof. However, it will be appreciated that those skilled in the art, upon consideration of this disclosure, may make modifications and improvements within the spirit and scope of this invention.

What is claimed is:

1. A method for repairing a bone having a fracture with a bone screw comprising an elongated tube having a first end, a second end and a tubular wall defining an interior opening extending from the first end to the second end, and a separate non-resorbable elongated holding element connected to the elongated tube at the second end, the elongated tube further comprises a bone thread on an outside surface of the tubular wall and the tubular wall comprising a plurality of recesses through the tubular wall to the interior opening forming a mesh-like open network, the method comprising:
    immersing the entire elongated tube into the bone; positioning the elongated tube across t he fracture; and
    attaching a fixation device to the holding element.

2. A method according to claim 1, wherein the fixation device comprises a plate or a marrow nail.

3. A method according to claim 1, further comprising:
    screwing a tip to the first end of the elongated tube;
    screwing the holding element to the second end of the elongated tube; and
    introducing the holding element into the bone when the elongated tube is fully introduced into the bone.

4. A method according to claim 3 further comprising applying a filler material into the interior opening of the elongated tube at a location adjacent the plurality of recesses.

5. A method according to claim 4, wherein the filler material is applied until it contacts the bone through the plurality of recesses.

6. A method according to claim 1, further comprising a tip connected to the first end of the elongated tube and wherein immersing the entire elongated tube into the bone includes immersing the entire tip into the bone.

7. The method according to claim 1, further comprising using the holding element as a driving tool to move a tip of the elongated tube across the fracture.

8. The method according to claim 1, further comprising:
    applying a filler material into the interior opening of the elongated tube of the bone screw; and
    then connecting the holding element to the elongated tube.

9. A method for repairing a bone having a fracture with a bone screw comprising an elongated tube having a first end, a second end and a tubular wall defining an interior opening extending from the first end to the second end, and an elongated holding element connected to the elongated tube at the second end, the elongated tube further comprises a bone thread on an outside surface of the tubular wall and the tubular wall comprising a plurality of recesses through the tubular wall to the interior opening forming a mesh-like open network, the method comprising:
    immersing the entire elongated tube into the bone;
    positioning the elongated tube across the fracture;
    attaching a fixation device to the holding element; and
    shortening the holding element.

10. A method for repairing a bone having a fracture with a bone screw comprising an elongated tube having a first end, a second end and a tubular wall defining an interior opening extending from the first end to the second end, and an elongated holding element connected to the elongated tube at the second end, the elongated tube further comprises a bone thread on an outside surface of the tubular wall and the tubular wall comprising a plurality of recesses through the tubular wall to the interior opening forming a mesh-like open network, the method comprising:
    immersing the entire elongated tube into the bone;
    positioning the elongated tube across the fracture;
    attaching a fixation device to the holding element
    removing the holding element from the elongated tube after the immersing step;
    applying a filler material into the interior opening of the elongated tube of the bone screw; and
    reconnecting the holding element to the elongated tube.

11. A method for repairing a bone having a fracture with a bone screw comprising an elongated tube having a first end, a second end and a tubular wall defining an interior opening extending from the first end to the second end, and an elongated holding element connected to the elongated tube at the second end, the elongated tube further comprises a bone thread on an outside surface of the tubular wall and the tubular wall comprising a plurality of recesses through the tubular wall to the interior opening forming a mesh-like open network, the method comprising:
    immersing the entire elongated tube into the bone;
    positioning the elongated tube across the fracture; and
    attaching a fixation device to the holding element by screwing a fastener to an end of the holding element to fasten the bone screw to the fixation device.

12. A method for repairing a bone having a fracture with a bone screw comprising an elongated tube having a first end, a second end and a tubular wall defining an interior opening extending from the first end to the second end, and an elongated holding element connected to the elongated tube at the second end, the elongated tube further comprises a bone thread on an outside surface of the tubular wall and the tubular wall comprising a plurality of recesses through the tubular wall to the interior opening forming a mesh-like open network, the method comprising:
    immersing the entire elongated tube into the bone;
    positioning the elongated tube across the fracture;
    attaching a fixation device to the holding element; and
    using the holding element as a driving tool to move a tip of the elongated tube across the fracture.

13. The method according to claim 12, further comprising:
    applying a filler material into the interior opening of the elongated tube of the bone screw; and
    then connecting the holding element to the elongated tube.

* * * * *